(12) United States Patent
Armentrout et al.

(10) Patent No.: US 7,327,132 B2
(45) Date of Patent: Feb. 5, 2008

(54) TESTING PROCEDURE FOR EVALUATING DIFFUSION AND LEAKAGE CURRENTS IN INSULATORS

(75) Inventors: Daniel Armentrout, Morrison, CO (US); Lucas Kumosa, Centennial, CO (US); Maciej Kumosa, Centennial, CO (US)

(73) Assignee: University of Denver, Denver, CO (US)

( * ) Notice: Subject to any disclaimer, the term of this patent is extended or adjusted under 35 U.S.C. 154(b) by 0 days.

(21) Appl. No.: 11/463,470

(22) Filed: Aug. 9, 2006

(65) Prior Publication Data

US 2007/0033989 A1 Feb. 15, 2007

Related U.S. Application Data

(60) Provisional application No. 60/708,133, filed on Aug. 15, 2005.

(51) Int. Cl.
*G01N 27/00* (2006.01)

(52) U.S. Cl. .................. 324/71.1; 324/557; 324/694

(58) Field of Classification Search ............... 324/71.1, 324/694, 557; 73/866
See application file for complete search history.

(56) References Cited

U.S. PATENT DOCUMENTS

| 3,258,634 | A | * | 6/1966 | Rich ................... 313/231.01 |
| 3,749,885 | A | * | 7/1973 | Nagasima ................ 219/522 |
| 4,992,201 | A | * | 2/1991 | Pearlman ................ 252/299.1 |
| 2004/0262730 | A1 | * | 12/2004 | Yamaji et al. ............. 257/678 |

* cited by examiner

*Primary Examiner*—Vincent Q. Nguyen
(74) *Attorney, Agent, or Firm*—Trego, Hines & Ladenheim, PLLC

(57) ABSTRACT

A method for predicting long-term electrical insulation properties of composite materials in a moist environment. The method including the steps of providing a specimen, and testing the specimen to determine moisture content values and leakage current values at predetermined time intervals. The method further including the steps of determining a moisture-leakage current factor from the moisture content values and leakage current values, and using the moisture-leakage current factor to determine electrical insulation properties of the specimen.

29 Claims, 7 Drawing Sheets

TESTING PROCEDURE FOR EVALUATING DIFFUSION AND LEAKAGE CURRENTS IN INSULATORS

CROSS-REFERENCE TO RELATED APPLICATIONS

This application claims the benefit of Provisional Application No. 60/708,133 filed on Aug. 15, 2005.

FIELD OF THE INVENTION

The present invention relates generally to the field of testing procedures for moisture absorption and leakage currents in composite materials. More specifically, the present invention discloses a testing procedure for predicting long-term electrical insulation properties of GRP composite materials based on short-term exposure to a moist environment.

BACKGROUND OF THE INVENTION

Glass-reinforced polymer (GRP) composites are widely used electrical insulators. GRP composite materials gradually absorb moisture over long periods of time when placed in a moist environment. The resulting leakage current can significantly impair the material's performance as an electrical insulator. In particular, there has previously been no practical way to predict the long-term electrical insulation properties of GRP composite materials in a moist environment.

In the past, the Applicants have performed high-voltage diffusion experiments utilizing a combination of the controlled moisture diffusion experiments and dielectric testing pursuant to ANSI Standard C29.11 Section 7.4.2 to evaluate the response of various glass reinforced polymer composites to moisture, and its effect on leakage current. For example, the tests were performed on solid composite rods by submerging them in boiling water and 0.1% NaCl solution for 100 hours and then measuring leakage currents. Despite the fact that very useful information was obtained about relationships between absorbed moisture and leakage currents in various unidirectional GRP composites with different surface conditions, no correlation was found between the mass gain and the leakage currents developed in the composites. Also, no attempt was made to correlate the rates of moisture absorption to the rates of increase in leakage current.

In another standard by ASTM D5229/D5229M-92 moisture absorption of materials can be measured using plates. Results for different materials can then be compared to either a Fickian single-phase model or non-Fickian double or multiple phase models. Also, a model was proposed by Carter and Kibler of anomalous diffusion that can be applied to handle non-Fickian diffusion (H. G. Carter and G. Kibler, "Langmuir-Type Model for Anomalous Moisture Diffusion in Composite Resins," *Journal of Composite Materials*, vol. 12, pp. 118-131, 1978).

In contrast to the prior art in this field, the present invention shows a linear relationship between moisture contents and changes in leakage currents. In addition, the thin-walled specimen geometry used in the present invention allows large moisture concentrations to be absorbed in short periods of time by different classes of dielectrics. This methodology allows measurement of leakage currents corresponding to different amounts of moisture contents absorbed by different classes of dielectrics. This methodology can also be used to predict the maximum moisture contents and maximum leakage currents in various classes of dielectrics absorbing moisture according to double-phase diffusion based on the Carter and Kibler model.

SUMMARY OF THE INVENTION

This invention provides a methodology for predicting the long-term electrical insulation properties of composite materials in a moist environment based on testing after short-term exposure to a moist environment. In particular, the present invention extrapolates long-term electrical insulation properties from measured leakage current after short-term exposure using various models, such as Fickian and non-Fickian diffusion models.

These and other advantages, features, and objects of the present invention will be more readily understood in view of the following detailed description and the drawings.

These and other objects of the present invention are achieved in the preferred embodiments disclosed below by providing a method for predicting long-term electrical insulation properties of composite materials in a moist environment. The method includes the steps of providing a specimen; testing the specimen to determine moisture content values and leakage current values at predetermined time intervals; determining a moisture-leakage current factor from the moisture content values and leakage current values; and using the moisture-leakage current factor to determine electrical insulation properties of the specimen.

According to another preferred embodiment of the invention, further including the step of determining moisture absorption properties of the specimen.

According to another preferred embodiment of the invention, further including the step of predicting a maximum moisture content, a maximum leakage current, and a time to saturation using an anomalous diffusion model.

According to another preferred embodiment of the invention, the moisture-current leakage factor is determined from a graph of change in leakage current values versus moisture content values.

According to another preferred embodiment of the invention, a linear relationship exists between the leakage current values and the moisture content values.

According to another preferred embodiment of the invention, further including the step of subjecting the specimen to a diffusible material.

According to another preferred embodiment of the invention, further including the step of subjecting the specimen to a high voltage.

According to another preferred embodiment of the invention, the voltage is ramped up to a maximum voltage of between 5 Volts per millimeter of specimen length and 500 Volts per millimeter of specimen length.

According to another preferred embodiment of the invention, a method for predicting long-term electrical insulation properties of composite materials in a moist environment, includes the steps of providing a composite material in the form of a hollow-core cylinder; subjecting the cylinder to a diffusible material; and measuring a moisture content of the cylinder at predetermined time intervals. The method further includes the steps of subjecting the cylinder to a high voltage and measuring a leakage current in the cylinder at the predetermined time intervals; determining a moisture-leakage current factor from the moisture content and leakage current; and correlating the moisture-leakage current factor to standardized data to determine electrical insulation properties of the specimen.

According to another preferred embodiment of the invention, further including the step of placing the cylinder in an environmental chamber and maintaining the cylinder at a constant temperature and a constant humidity.

According to another preferred embodiment of the invention, further including the step of weighing the cylinder to determine the moisture content.

According to another preferred embodiment of the invention, further including the step of measuring an initial mass of the cylinder prior to subjecting the cylinder to the diffusible material.

According to another preferred embodiment of the invention, further including the step of measuring an initial leakage current of the cylinder prior to subjecting the cylinder to the diffusible fluid.

According to another preferred embodiment of the invention, the diffusible fluid is selected from the group consisting of water, liquid metal, liquid solutions, and vapors.

According to another preferred embodiment of the invention, a method for predicting long-term electrical insulation properties of composite materials in a moist environment includes the steps of providing a composite material in the form of a hollow-core cylinder; recording an initial mass of the cylinder; recording an initial leakage current of the cylinder; and placing the cylinder in an environmental chamber. The method further includes the steps of subjecting the cylinder to a diffusible fluid; removing the cylinder from the environmental chamber at predetermined time intervals and recording a mass and a leakage current of the cylinder; determining a moisture content of the cylinder from the mass of the cylinder; determining a moisture-leakage current factor from the moisture content and leakage current; and using the moisture-leakage current factor to determine electrical insulation properties of the specimen.

According to another preferred embodiment of the invention, further including the step of placing the cylinder in a high voltage chamber and subjecting the cylinder to a high voltage.

According to another preferred embodiment of the invention, further including the step of subjecting the cylinder to a high voltage.

According to another preferred embodiment of the invention, the temperature is maintained at about 50 degrees Celsius and the humidity is maintained at about 80 percent relative humidity.

According to another preferred embodiment of the invention, further including the step of correlating a rate of moisture absorption to a rate of increase in leakage currents using the equation $I_{L(AC)}(t) = F_{M-LC} \cdot M(t)$.

According to another preferred embodiment of the invention, the cylinder has a length of about 0.1 millimeters to about 50 millimeters.

According to another preferred embodiment of the invention, the cylinder has an outside diameter of about 2 millimeters to about 100 millimeters.

According to another preferred embodiment of the invention, the cylinder has an inside diameter of about 1 millimeter to about 99 millimeters.

According to another preferred embodiment of the invention, the cylinder has a length of about 30 millimeters and an external diameter of about 15.9 millimeters.

According to another preferred embodiment of the invention, the cylinder has a wall thickness selected from the group consisting of 1 millimeter, 2 millimeters, and 4 millimeters.

According to another preferred embodiment of the invention, further including the step of placing the cylinder between two electrodes.

According to another preferred embodiment of the invention, further including the step of subjecting the cylinder to a high voltage.

According to another preferred embodiment of the invention, the electrodes are brass.

BRIEF DESCRIPTION OF THE DRAWINGS

The present invention can be more readily understood in conjunction with the accompanying drawings, in which.

DETAILED DESCRIPTION OF THE INVENTION

Figure 1:
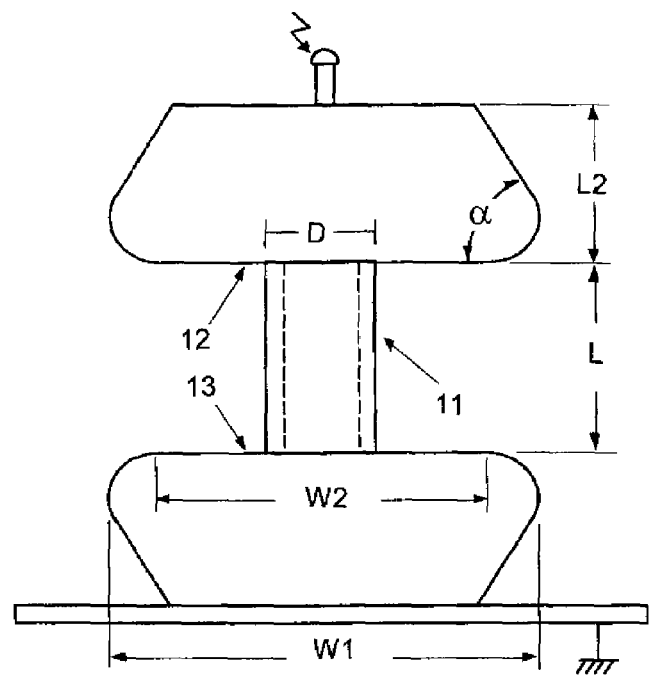
FIG. 1 is a diagram of the high voltage test setup for measuring leakage currents.

This invention relates to high-voltage diffusion experiments utilizing a combination of controlled diffusion and dielectric testing to evaluate the response of dielectric materials to the diffusion of a fluid (liquid or vapor) and its effect on leakage current. Using this invention, for example, the rate of moisture absorption can be correlated to the rates of increase in leakage currents in composite high-voltage insulators based on different polymers and glass fibers. Diffusion can be characterized based either on Fickian or non-Fickian models. However, the present invention can be used for numerous other applications.

Moisture Diffusion Analysis. The moisture diffusion process for most unidirectional composites is assumed to be Fickian in nature. This means that the diffusion of moisture into the material follows Fick's second law, which is also the same law that governs heat conductivity. Fick's second law states:

$$\frac{\partial c}{\partial t} = D_x \frac{\partial^2 c}{\partial x^2} \quad (1)$$

where c is the concentration of moisture, t is time, x is distance through the transverse direction of a specimen and $D_x$ is the coefficient of diffusivity in the transverse direction. Using the appropriate boundary conditions, a relationship between the moisture content at any time (M), the maximum moisture content ($M_{MAX}$) of a specimen, its thickness (h), and the diffusivity constant ($D_x$) is given as:

$$M = M_{MAX}\left[1 - \exp\left(-7.3\left(\frac{D_x \cdot t}{h^2}\right)^{0.75}\right)\right] \quad (2)$$

where both $M_{MAX}$ and $D_x$ can be obtained from moisture content/weight gain versus square root of time plots. This is done by using the following equation:

$$D_A = \pi\left(\frac{h}{4M_{MAX}}\right)^2 \cdot \left(\frac{M_2 - M_1}{\sqrt{t_2} - \sqrt{t_1}}\right)^2 \quad (3)$$

assuming that the apparent diffusivity, $D_A$, is approximately equal to the transverse diffusivity, $D_x$. In equation 3, $M_{MAX}$ is the average equilibrium value on the curve and the term $$\left(\frac{M_2 - M_1}{\sqrt{t_2} - \sqrt{t_1}}\right)$$

is equal to the slope of the initial linear segment of the moisture content/weight gain versus $\sqrt{t}$ curves. For more detailed information on the application of the Fickian diffusion numerical prediction, the reader is referred to C.-H. Shen and G. S. Springer, "Moisture Absorption and Description of Composite Material," *Journal of Composite Materials*, vol. 10, pp. 2-20, 1976. The values for percent moisture content at any time can be determined using:

$$M = \frac{\text{weight of moist specimen} - \text{weight of dry specimen}}{\text{weight of dry specimen}} \times 100\% \quad (4)$$

The behavior of materials in a moist environment depends greatly on the conditions of that environment. Materials in an environment with constant humidity but varying temperatures show the same level of maximum moisture absorption, but the rates of absorption differ. A specimen in a cooler environment will take more time to equilibrate than a specimen in a warmer environment. In constant temperature, but with varying amounts of humidity, the rates of water absorption stay the same, but the total amount of moisture absorbed increases with an increase in ambient humidity.

Not only do environmental variables impact the moisture absorption curves, but so do material properties like dissolution, micro-cracking, molecular binding, or structural relaxation. These phenomena deviate from single-phase Fickian diffusion and therefore cannot be accurately analyzed using the numerical procedure presented. A multiple-phase model is therefore needed.

Anomalous Diffusion Analysis. The analysis presented in the previous section deals with single phase diffusion where there is only one phase of moisture uptake followed by equilibrium. Anomalous diffusion implies numerous different phases of moisture absorption leading to a final equilibrium. The behavior of some of the composite materials investigated in this research has been previously found to be anomalous (non-Fickian). This type of diffusion cannot be readily analyzed using the single-phase methods presented above. A multi-phase diffusion model is needed which describes the physical behavior of the material.

One such model was presented by Carter and Kibler. This model uses the assumption that moisture in materials with anomalous (two-phase) diffusion occurs in two distinct yet related phases. The first is the absorption of water molecules in the mobile phase into the material with a diffusion coefficient $D_\Gamma$. Next, the molecules are bound to the molecular structure of the resin with a probability $\Gamma$ and become unbound with a probability B. Using these assumptions, Carter and Kibler devised a model for the analysis of moisture absorption in materials with anomalous diffusion characteristics. A convenient approximation of this model is presented below:

$$M = M_{MAX}\left(\frac{B}{\Gamma + B}e^{-\Gamma t}\left[1 - \frac{8}{\pi^2}\sum_{l=1}^{\infty(odd)}\frac{e^{-\kappa l^2 t}}{l^2}\right] + \frac{B}{\Gamma + B}(e^{-Bt} - e^{-\Gamma t}) + (1 - e^{-Bt})\right) \quad (5)$$

where:

$2\Gamma, 2B \ll \kappa$ and:

$\kappa = \pi^2 D_\Gamma/(h)^2$

The value of $D_\Gamma$ can be assumed from simple single-phase diffusion in equation (3). The necessary $M_{MAX}$ value used to calculate $D_\Gamma$ is assumed to give the best possible fit for the initial slope and first knee in the moisture content versus square root of time curves, up to the second phase of diffusion.

Testing Apparatus. One embodiment of the testing apparatus used in the present invention is shown in FIG. 1. Hollow-core cylinders 11 of various dielectric materials are machined from solid cylinders or prepared as tubes. The test specimens 11 are then subjected to moisture or other diffusible material (e.g., water, liquid metal, liquid solutions or vapors), so that the specimens 11 contain various amounts of the diffused material. Then, the leakage currents in the specimens 11 are measured by placing the tubular specimens 11 between two electrodes 12 and 13, as shown in FIG. 1. Subsequently, the changes in leakage currents are related to the amount of the absorbed diffused material.

For example, in the case of composite insulators based on solid rods with rod diameters ranging from a few millimeters to 100 mm, the moisture absorption experiments can be conducted in moist environments ranging from humid air to liquid immersion, and a temperature range from room temperature to boiling temperature. The voltage range can be from approximately 0 to 100 kV with the ramp rate ranging from about 0 to 15 kV/sec. The ranges for the specimen 11 geometry could be: an external cylinder diameter ranging from about 2 mm to 100 mm; an internal diameter from about 1 mm to 99 mm; and the length of the cylinder ranging from about 0 to 50 mm.

If the diffusion of the material is Fickian (single-phase diffusion), the maximum content of the absorbed material and the maximum leakage current will be measured directly. In the case of double-phase non-Fickian diffusion with the full saturation requiring very long times of exposure (e.g., several years), a numerical procedure based on the Carter and Kibler model can be used. Then the maximum leakage current can also be estimated based on this numerical procedure.

Experimental Studies. For example, the experimental data discussed below is based on thin-walled hollow-core composite cylinders 11 made up of ECR (low seed)-glass fibers and epoxy subjected to moisture. The preferred specimen 11 geometry would be a length "L" of about 30±0.5 mm with an external diameter "D" of about 15.9±0.1 mm. The wall thicknesses of the cylinders 11 in the experimental data provided below were 1, 2 and 4 mm. The dimensions of the electrodes 12 and 13 and distances in FIG. 1 are: "W1"=64±0.1 mm, "W2"=50±0.1 mm, "L2"=25±0.1 mm and "α"=60°±1°. All of the dimensions follow ANSI standard C29-11.

Using this technique, the rates of moisture absorption can be correlated to the rates of increase in leakage currents in hollow core cylinders 11 made up of ECR (low seed)-glass fibers and epoxy under controlled moisture diffusion conditions pursuant to ASTM Standard D5229/D5229M-92. Since moisture absorption by the ECR (low seed)-glass/epoxy composite is non-Fickian in nature and can not be accurately described using single-phase models, an anomalous diffusion (double phase) model can be applied to the experimental results. For example, a methodology based on the model for anomalous diffusion disclosed by H. G. Carter and G. Kibler, "Langmuir-Type Model for Anomalous Moisture Diffusion in Composite Resins," *Journal of Composite Materials*, vol. 12, pp. 118-131, 1978, can be used to handle non-Fickian diffusion in insulator composites for various specimen thicknesses.

The effect of moisture on the measured leakage currents in the composite was also investigated using the hollow core composite cylinders 11. Despite some scatter observed in the experimental data, a linear relationship was noticed between the amount of moisture in the ECR (low seed)-glass/epoxy composite and the level of AC leakage current. The linear trends in the change in AC leakage current versus moisture content plots allowed for accurate predictions of the electrical insulation properties. Therefore, using Carter and Kibler's model, the maximum moisture content, maximum leakage current and time-to-saturation for the composite can be subsequently predicted. We could relate the ability to predict moisture absorption, M(t), with change in leakage current, $I_{L(AC)}$, using the following equation:

$$I_{L(AC)}(t) = F_{M-LC} \cdot M(t) \quad (6)$$

where $F_{M-LC}$ is the moisture/leakage current factor. Both single-phase Fickian and anomalous moisture diffusion models can be used for this relationship. More importantly the predictions of moisture absorption and leakage currents could be made based on relatively short term moisture data even if the diffusion process in the composites is anomalous in nature with long times required for full saturation.

The hollow core cylinder testing under controlled moisture and high voltage conditions has the potential to become a standard screening test for selecting suitable glass/polymer composites for insulator applications. By measuring the moisture-leakage current factors, different insulator core composites can be ranked for their electrical response under moisture as a function of in-service conditions. The present invention attempts to demonstrate this by comparing the ECR (low seed)-glass/epoxy system with another one based on the ECR (high seed)-glass fibers embedded in a modified polyester resin.

For the electrical testing performed in this work, two materials were chosen. ECR (low seed)-epoxy was picked for its excellent resistance to stress corrosion cracking provided by the ECR-glass fibers, and its acceptable behavior in the presence of moisture. The epoxy resin does not absorb moisture too fast, as in the case of the modified polyester material, but it does have a tendency to not fully equilibrate with its surroundings right away like the vinyl ester and modified polyester materials do. ECR (high seed)-glass/modified polyester, on the other hand, was chosen for its poor moisture absorption properties. No previous evidence of anomalous diffusion has been found regarding this material.

The hollow core cylinders 11 were machined from 15.9 mm diameter unidirectional pultruded rods of various lengths obtained from Glasforms, Inc. Then, 30±0.5 mm long pieces were cut from these rods and a 7.9 mm pilot hole was drilled out of the center. This produced eighteen hollow cylinders with 4 mm thick walls. Six of these were cleaned and set aside, while the other twelve were then placed in a lathe and the centers were bored out to the desired diameters. The cutting on the lathe was performed in two steps. First one side was cut, halfway through the specimen, and then the other side was also cut to match the first. This was done in an attempt to minimize the cracking of the composite, especially in the thin 1 mm thick walled specimens. As a result, eighteen specimens were prepared (nine per material), with 1, 2 and 4 mm wall thickness, three specimens for each wall thickness.

After machining, the specimens 11 were thoroughly cleaned and dried at 60° C. Subsequently, the initial mass and the initial leakage currents of the specimens 11 were recorded just after drying. Then, the specimens 11 were placed into an environmental chamber and maintained at a temperature between 20° C. and 100° C. and a relative humidity of between 10 percent and 100 percent. In this case, the specimens 11 were maintained at 50° C. and 80% relative humidity. The mass of the specimens 11 was measured at increasing time intervals using an analytical balance with a readability of 0.1 mg. To ensure that the specimens 11 did not spend more than 30 minutes outside of the environmental chamber thus affecting moisture data, three specimens at a time were weighed. The specimens 11 were weighed at changing time intervals due to the considerable slow-down in moisture uptake for a period of approximately 4 months. After each weighing the specimens 11 were tested for their electrical properties as described in the next section.

Figure 2:
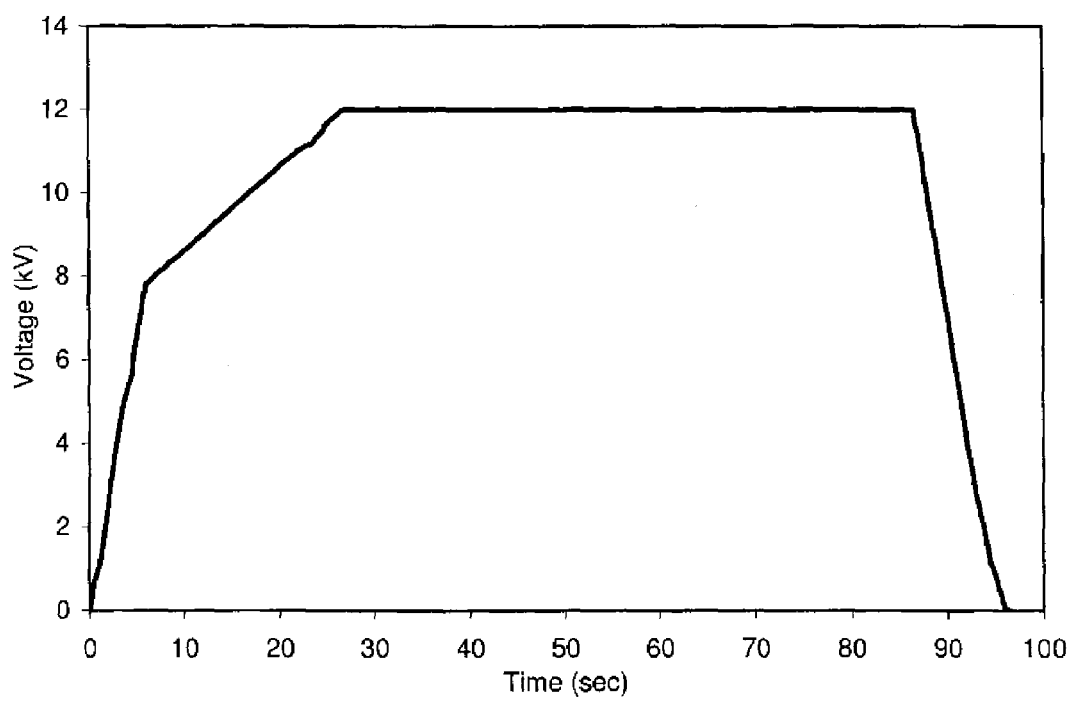
FIG. 2 is a graph showing a typical voltage versus time response for a leakage current test.

During high-voltage testing, the composite cylinders 11 were placed between two brass electrodes 12 and 13 in a high voltage chamber as shown in FIG. 1. The ANSI standard calls for the voltage to ramp at approximately 1 kV/s to 12 kV. The voltage is ramped up to a maximum voltage of between 5 Volts per millimeter of specimen length and 500 Volts per millimeter of specimen length. The unit was set at the maximum voltage ramp rate and set to stop at 12 kV, yielding the initial voltage time curve shown in FIG. 2. A Protek 608 digital multi-meter, with a 0.1 µA resolution on the 5 mA scale, was used to record all AC maximum leakage current values. During testing, a dry standard specimen that was kept inside the high voltage chamber was tested for its AC leakage current at the beginning and at the end of each testing session to give us some indication of the change in ambient conditions for each testing session. These changes in ambient conditions shown through the standard specimen were then subtracted from the data analysis presented later.

Figure 3:
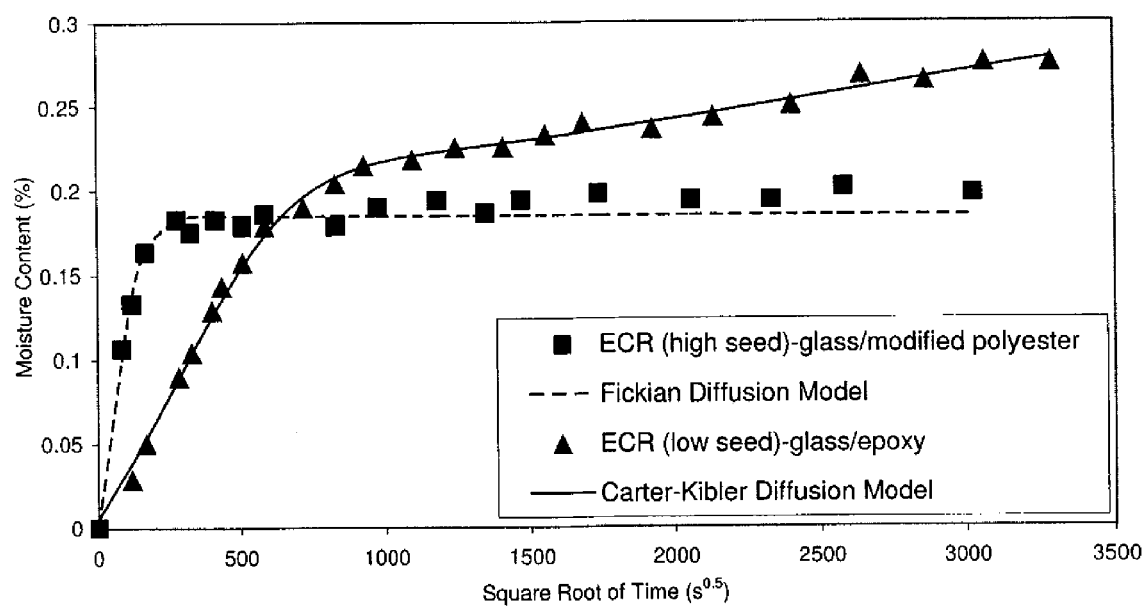
FIG. 3 is a graph showing examples of moisture absorption versus the square root of time (actual and predicted) for the ECR (high seed)-glass/modified polyester and ECR (low seed)-glass/epoxy hollow core cylinders with 1-mm wall thickness.

The most important results from the moisture and leakage current experiments for the ECR (high seed)-glass/modified polyester and ECR (low seed)-glass/epoxy composites tested in the 1, 2 and 4 mm thick cylinders 11 are shown in Tables 1a and 1b. Also, as examples, the moisture absorption vs. square root of time curves for one 1-mm thick ECR (low seed)-glass/epoxy specimen and one 1-mm thick ECR (high seed)-glass/modified polyester 1 mm thick specimen are shown in FIG. 3. In addition to the experimental data, the fits according to the single diffusion model and the non-Fickian diffusion are also plotted in FIG. 3. It can be observed in this figure that the modified polyester based specimen reached saturation after approximately 4 days of moisture exposure. However, in the case of the epoxy based system no saturation was achieved after almost 3 months of testing. Very similar behavior of the two composite systems was observed in the other 1 mm thick, and 2 and 4 mm thick specimens with all epoxy specimens steadily absorbing moisture without saturation and all modified polyester based cylinders reaching saturation in relatively short periods of time.

Figure 4A:
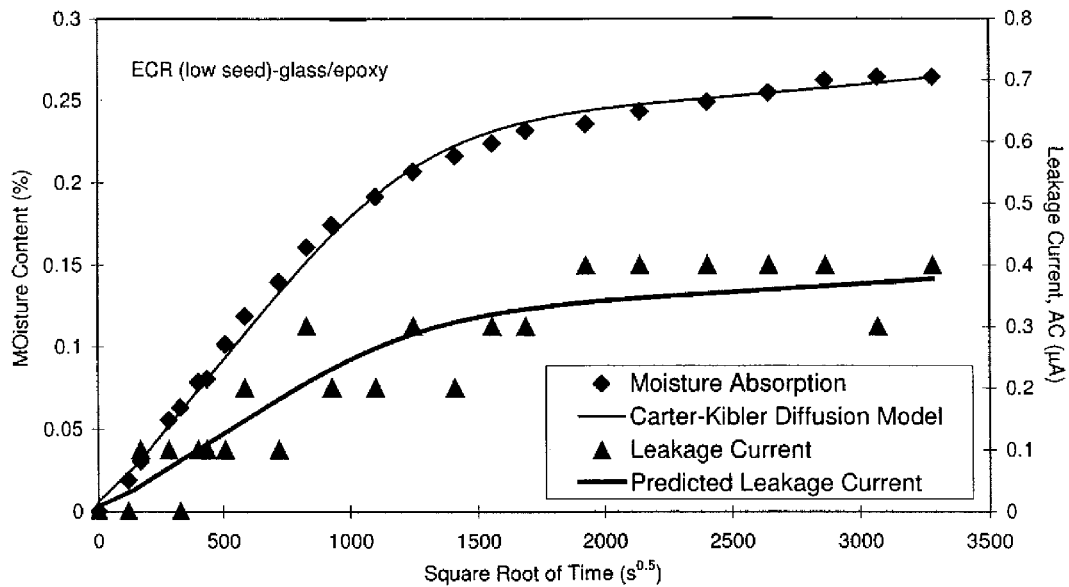
FIGS. 4a and 4b are graphs showing examples of leakage current and moisture contents versus the square root of time (actual and predicted) for the ECR (low seed)-glass/epoxy in FIG. 4a, and ECR (high seed)-glass/modified polyester in FIG. 4b for hollow core cylinders with 2-mm wall thickness.
Figure 4B:
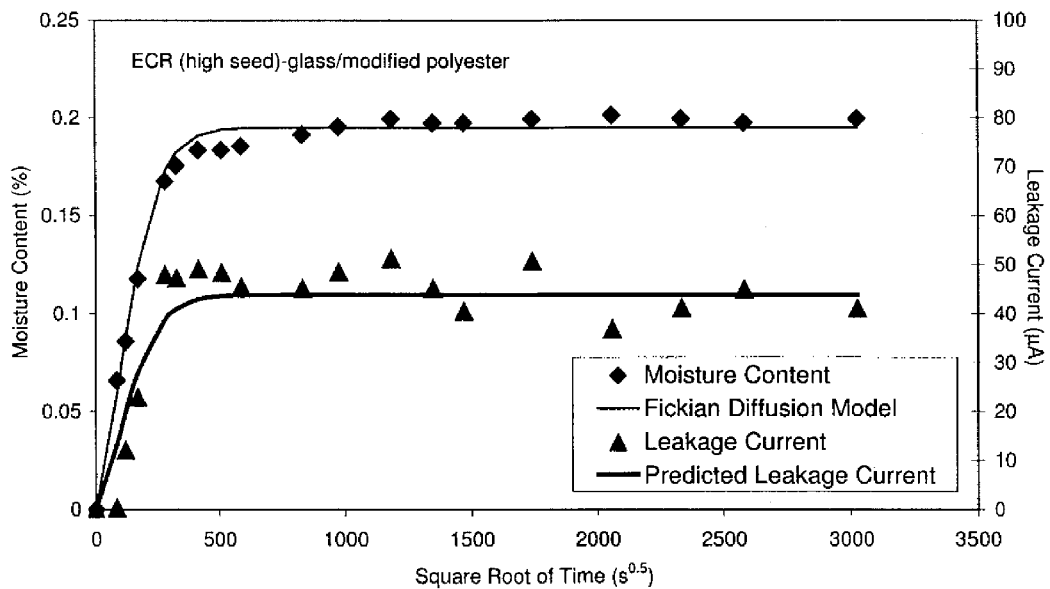

The leakage current versus square root of time curves for one 2-mm thick ECR (low seed)-glass/epoxy cylinder and one 2-mm thick ECR (high seed)-glass/modified polyester are presented in FIGS. 4a and 4b, respectively as examples. The corresponding moisture absorption curves are also shown in these figures. In addition to the experimental moisture and leakage current data, the corresponding fits according to the Fickian and anomalous diffusion models are also shown in FIGS. 4a and 4b both for the moisture and the leakage current results. Very similar relations were observed for the two composite systems tested using the 1 and 4 mm thick specimens.

For the epoxy-based composites the rate of moisture absorption, $k_M$, and the diffusion coefficient, $D_A$, listed in Table 1a were determined experimentally from the initial portions of the moisture contents versus square root of time curves. However, the maximum moisture contents and the times to saturations as well as the maximum leakage currents were estimated using the procedures in accordance with the Carter and Kibler non-Fickian diffusion model. Since the modified polyester based specimens reached saturation, the maximum moisture contents and maximum leakage currents could be determined directly from the moisture and high voltage experiments. Also, the rates of moisture absorption ($k_M$) and the diffusion coefficients ($D_A$) shown in Table 1b were determined directly from the moisture content vs. square root of time curves.

Table 1a below shows values of the initial rate of moisture absorption ($k_M$), diffusion coefficient ($D_A$) and predicted values of maximum moisture content ($M_{MAX}$), moisture-leakage current factor ($F_{M-LC}$), maximum leakage current ($I_{L(AC)-MAX}$) and time to 99% of saturation ($t_{SAT}$) for the ECR (low seed)-glass/epoxy composite specimens.

| Wall Thickness (mm) | Specimen # | $k_M$ (10$^{-4}$ % weight gain/(s) | DA (10-7) [mm2/s]* | MMAX (%)** | IL(AC)-MAX (µA)** | $F_{M-LC}$ (µA/%) | $t_{SAT}$ (years)** |
|---|---|---|---|---|---|---|---|
| 1 | 1 | 3.20 | 4.15 | 0.34 | 0.71 | 2.06 | 1.98 |
|   | 2 | 3.04 | 3.75 | 0.35 | 0.47 | 1.35 | 1.98 |
|   | 3 | 2.98 | 3.60 | 0.34 | 0.60 | 1.74 | 1.98 |
| 2 | 1 | 1.84 | 4.62 | 0.36 | 0.50 | 1.40 | 3.20 |
|   | 2 | 2.06 | 6.23 | 0.35 | 0.82 | 2.37 | 3.20 |
|   | 3 | 1.88 | 5.22 | 0.34 | 0.62 | 1.80 | 3.20 |
| 4 | 1 | 1.09 | 5.94 | 0.37 | 0.73 | 1.98 | 7.94 |
|   | 2 | 1.04 | 5.47 | 0.37 | 0.94 | 2.51 | 7.94 |
|   | 3 | 1.07 | 5.72 | 0.37 | 0.93 | 2.55 | 7.94 |

*The value of $D_A$ is calculated for the first diffusion phase.
**The values of $M_{MAX}$, $I_{L(AC)-MAX}$ and $t_{SAT}$ are predicted values based on the Carter-Kibler model for anomalous diffusion.

Table 1b below shows values of the initial rate of moisture absorption ($k_M$), diffusion coefficient ($D_A$) and predicted values of maximum moisture content ($M_{MAX}$), moisture-leakage current factor ($F_{M-LC}$), maximum leakage current ($I_{L(AC)-MAX}$) and time to 99% of saturation ($t_{SAT}$) for the ECR (high seed)-glass/modified polyester composite specimens.

| Wall Thickness (mm) | Specimen # | $k_M$ (10$^{-4}$ % weight gain/$\sqrt{s}$) | $D_A$ (10$^{-7}$) [mm$^2$/s] | $M_{MAX}$ (%) | $I_{L(AC)-MAX}$ (µA) | $F_{M-LC}$ (µA/%) | $t_{SAT}$ (days) |
|---|---|---|---|---|---|---|---|
| 1 | 1 | 11.33 | 69.8 | 0.189 | 37.0 | 195.7 | 4 |
|   | 2 | 11.09 | 66.9 | 0,192 | 43.5 | 226.4 | 4 |
|   | 3 | 12.81 | 84.7 | 0.196 | 46.8 | 239.0 | 4 |

-continued

| Wall Thickness (mm) | Specimen # | $k_M$ ($10^{-4}$ % weight gain/$\sqrt{s}$) | $D_A$ ($10^{-7}$) [mm²/s] | $M_{MAX}$ (%) | $I_{L(AC)\text{-}MAX}$ (µA) | $F_{M\text{-}LC}$ (µA/%) | $t_{SAT}$ (days) |
|---|---|---|---|---|---|---|---|
| 2 | 1 | 6.72 | 93.4  | 0.197 | 51.4 | 261.1 | 8 |
|   | 2 | 7.42 | 108.1 | 0.201 | 24.8 | 123.4 | 8 |
|   | 3 | 6.93 | 99.3  | 0.198 | 44.5 | 224.9 | 8 |
| 4 | 1 | 4.53 | 146.2 | 0.215 | 54.4 | 252.7 | 16.2 |
|   | 2 | 4.26 | 135.8 | 0.207 | 45.6 | 220.2 | 16.2 |
|   | 3 | 4.59 | 143.0 | 0.216 | 62.9 | 291.3 | 16.2 |

Figure 5A:
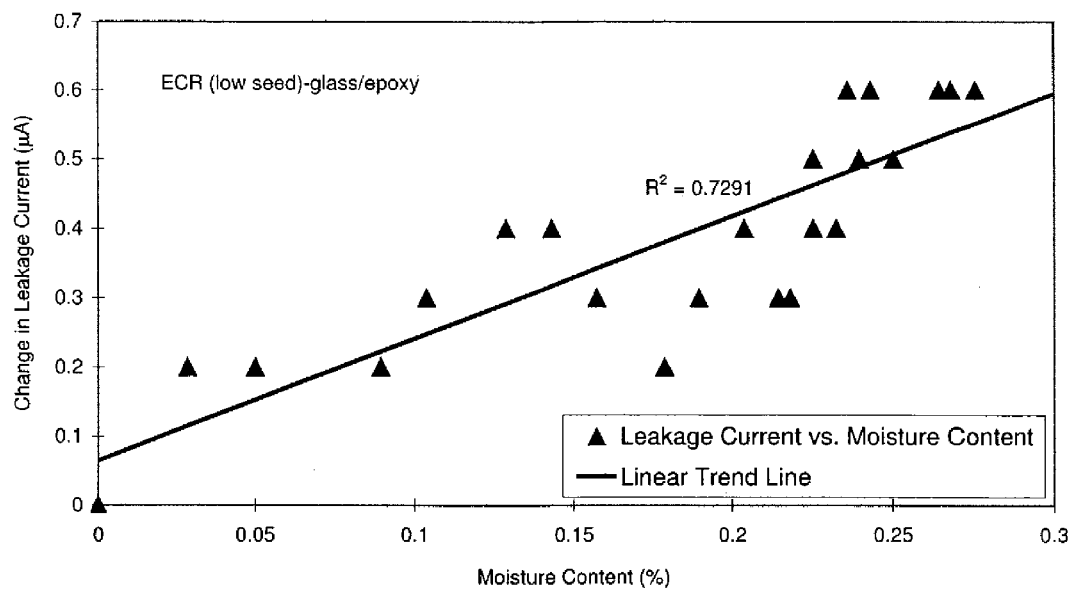
FIGS. 5a and 5b are graphs showing the change in AC leakage current versus moisture content for a 1-mm thick ECR (low seed)-glass/epoxy specimen in FIG. 5a, and a ECR (high seed)-glass/modified polyester specimen in FIG. 5b.
Figure 5B:
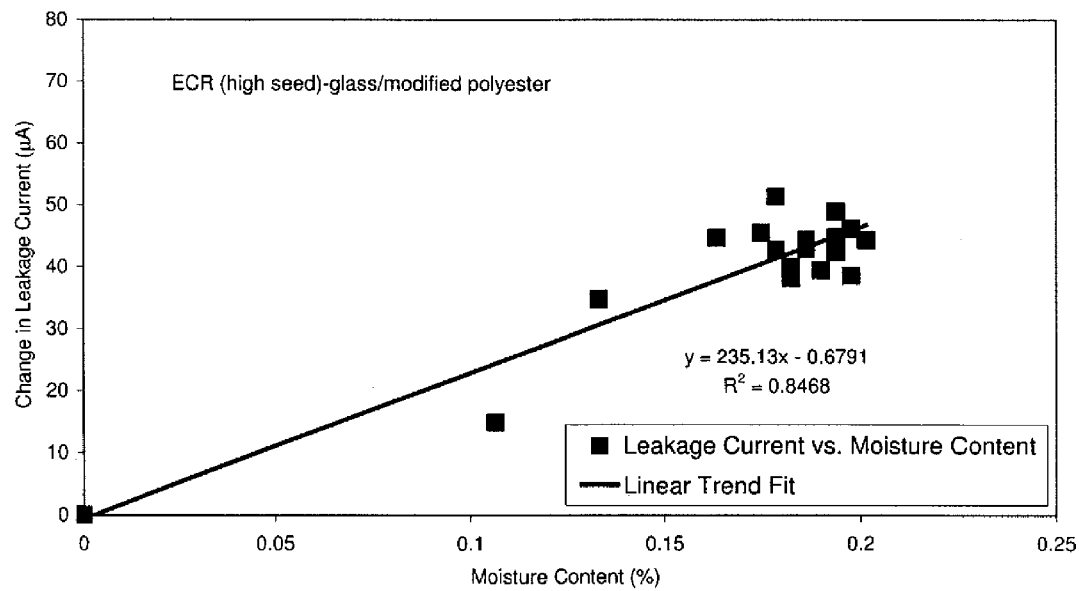
Figure 6A:
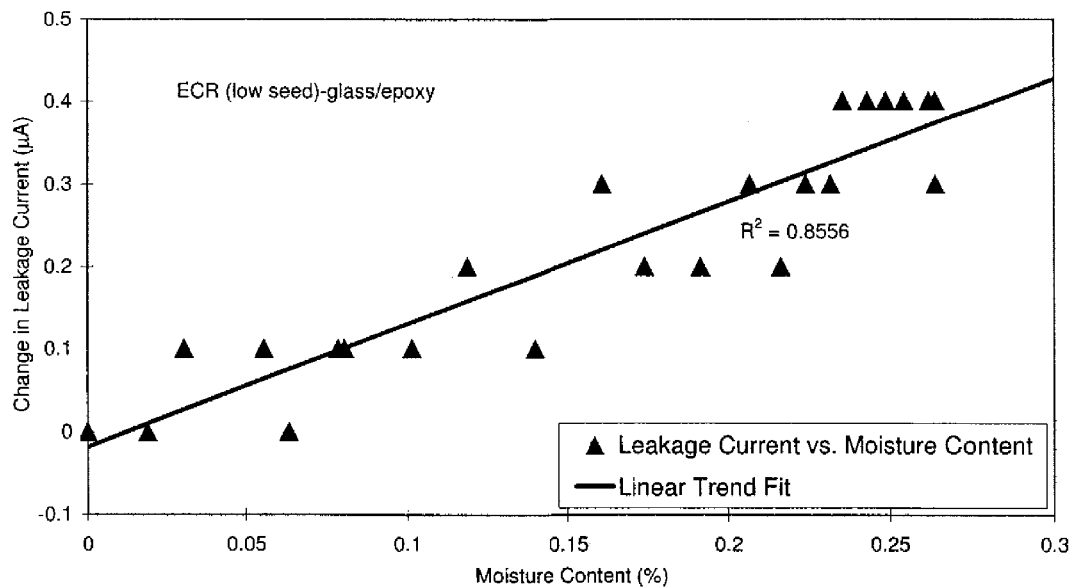
FIGS. 6a and 6b are graphs showing the change in AC leakage current versus moisture content for a 2-mm thick ECR (low seed)-glass/epoxy specimen in FIG. 6a, and a ECR (high seed)-glass/modified polyester specimen in FIG. 6b.
Figure 6B:
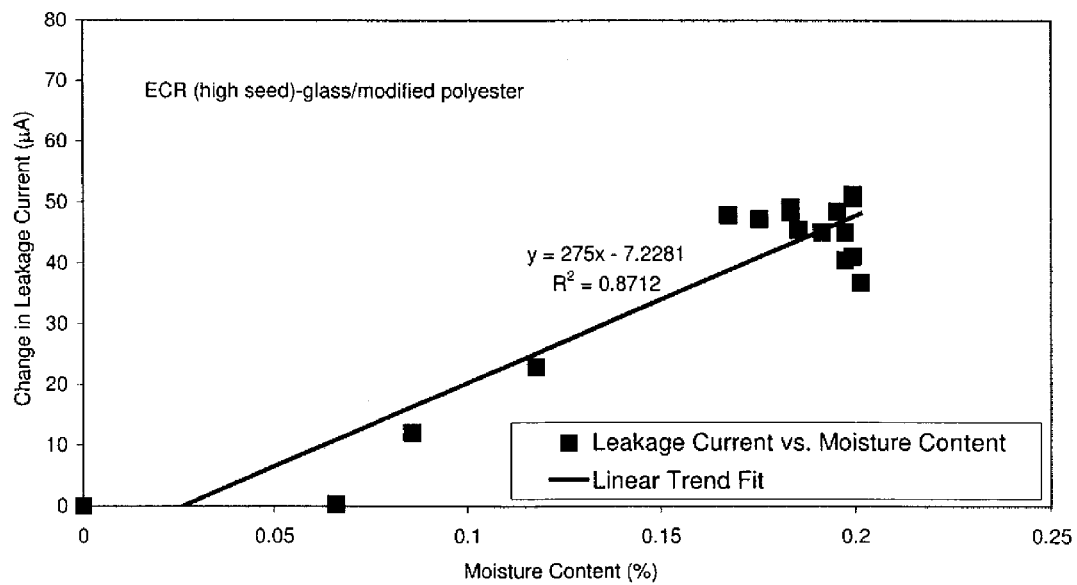
Figure 7A:
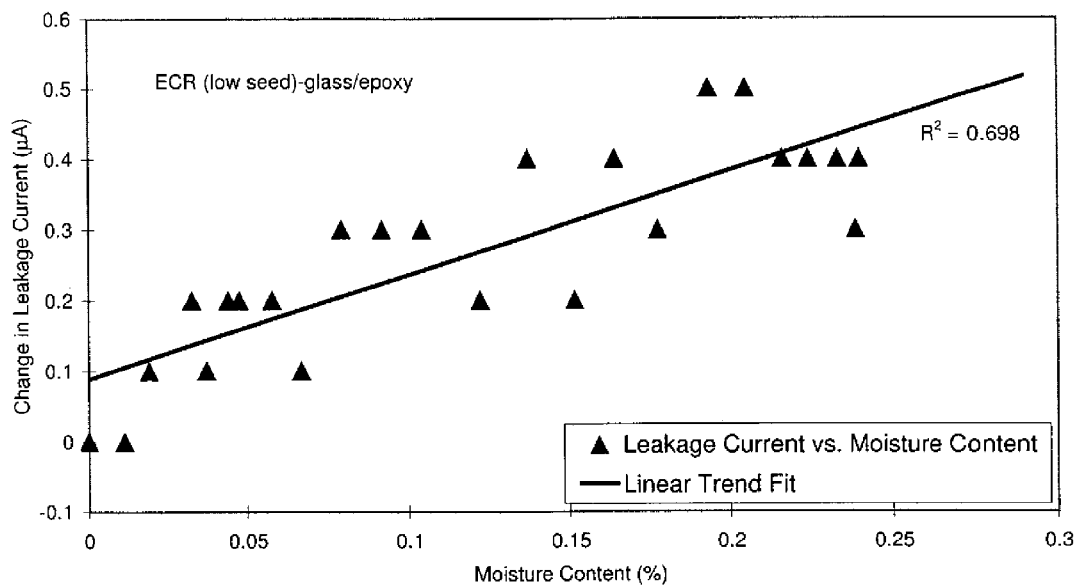
FIGS. 7a and 7b are graphs showing the change in AC leakage current versus moisture content for a 4-mm thick ECR (low seed)-glass/epoxy specimen in FIG. 7a, and a ECR (high seed)-glass/modified polyester specimen in FIG. 7b.

The moisture/leakage current factors, $F_{M-LC}$, listed in Tables 1a and 1b were determined from the change in AC leakage currents vs. moisture content plots obtained for each specimen. Some of these plots are presented for individual randomly selected specimens per wall thickness and material. The plots for the 1-mm thick ECR (low seed)-glass/epoxy and 1-mm thick ECR (high seed)-glass/modified polyester specimens are presented in FIGS. 5a and 5b, respectively whereas in FIGS. 6a and 6b the plots from the 2-mm thick specimens are shown. Finally, the plots from the 4-mm thick ECR (low seed)-glass/epoxy and ECR (high seed)-glass/modified polyester specimens are illustrated in FIGS. 7a and b, respectively.

Several important observations can be made from analyzing these plots. First, all six plots show distinct linear trends between change in AC leakage currents and absorbed moisture. Second, the thinner specimens 11 show more scatter due to the fact that these specimens 11 reach equilibrium quicker, not providing enough data between the beginning of the test and full moisture saturation. Also, the ECR (low seed)-glass/epoxy specimens 11 show more scatter than the ECR (high seed)-glass/modified polyester materials due to their much smaller leakage current values.

Figure 7B:
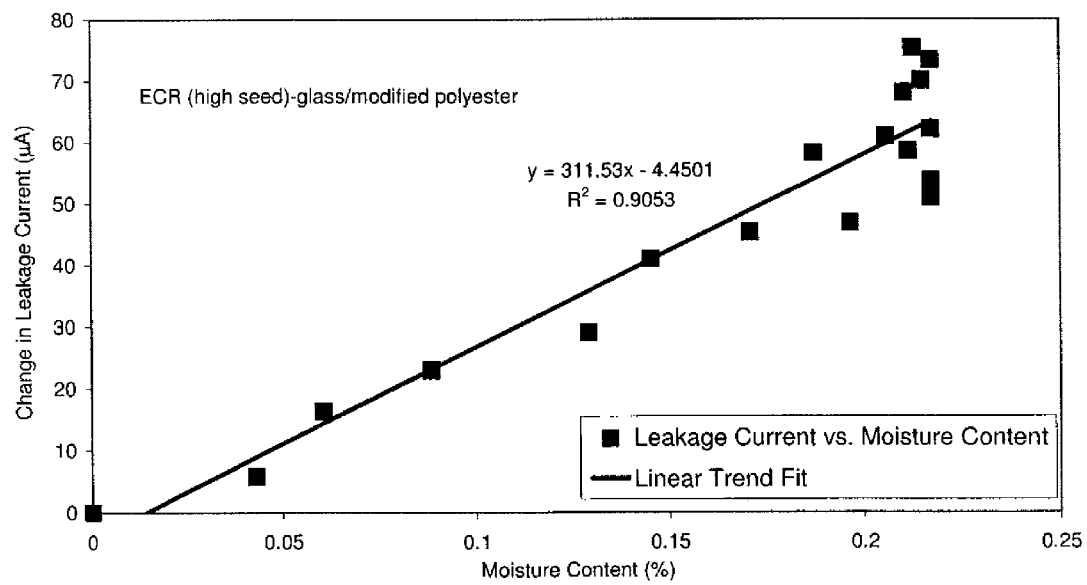

It can also been seen in FIGS. 5-7 that for very similar amounts of total absorbed moisture (about 0.20%), the ECR (high seed)-glass/modified polyester specimens exhibited maximum change in leakage currents in the range of 50-70 µA, whereas the ECR (low seed)-glass/epoxy material never exceeded 0.7 µA. The difference in slope of the change in AC leakage current vs. moisture content plots between the ECR (low seed)-glass/epoxy and ECR (high seed)-glass/modified polyester materials is approximately 150-200 times. This is the reason why the moisture/leakage current factors, $F_{M-LC}$, listed in Tables 1a and 1b are so different for the epoxy and the modified polyester based specimens 11.

Figure 8A:
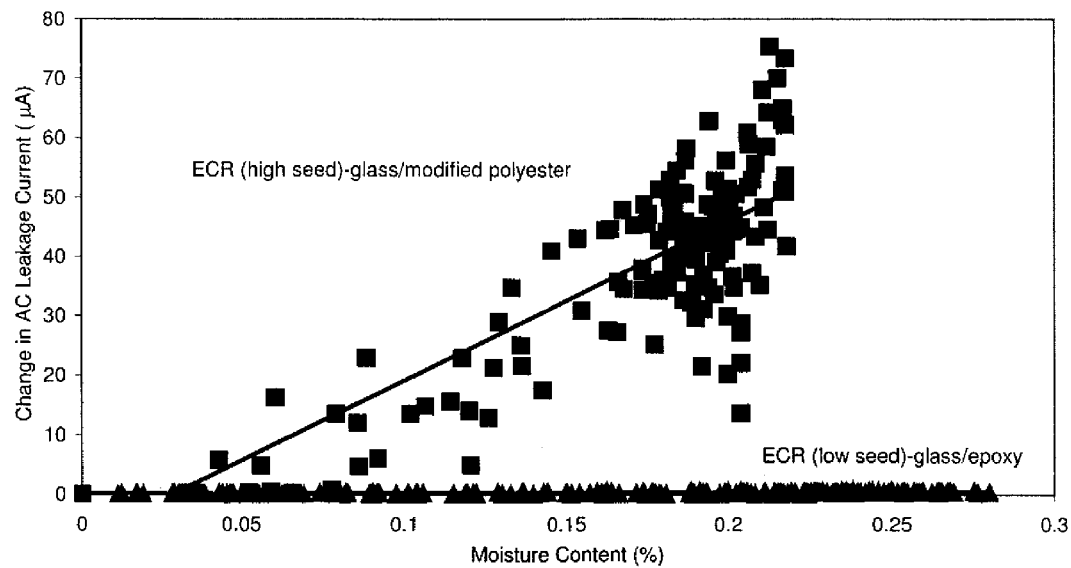
FIGS. 8a and 8b are graphs showing the change in AC leakage current versus moisture content plotted on linear (FIG. 8a) and semi-log (FIG. 8b) scales with linear trend fits for all data points for FIG. 8a and for all non-zero data points for FIG. 8b from ECR (low seed)-glass/epoxy and ECR (high seed)-glass/modified polyester specimens.
Figure 8B:
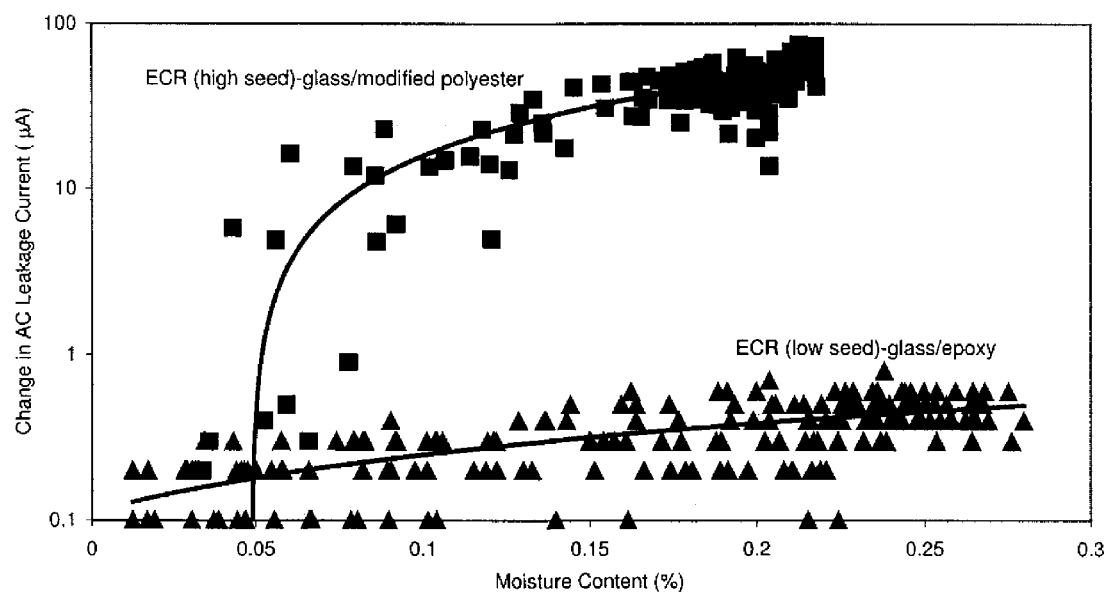

Clearly, the two composite systems have responded very differently to moisture and high voltage. The final comparison between the two composite systems was made in FIGS. 8a and 8b. In FIG. 8a the change in AC leakage currents versus moisture content plots of all the data points per material are shown. This same data plotted on a semi-log scale is presented in FIG. 8b. These two figures illustrate very well the extreme difference in the electrical behavior of these two composites when exposed to similar levels of absorbed moisture. It is clear that ECR (low seed)-glass/epoxy is much better suited for electrical insulation applications in moist environments, whereas ECR (high seed)-glass/modified polyester should be avoided, especially if there is a much greater concentration of ambient moisture than present in these tests.

The high leakage currents developed in the ECR (high seed)-glass/modified polyester system were caused by the presence of seeds in the ECR-glass fibers. The presence of the seeds causes higher leakage currents in composites based on high seed ECR-glass fibers in comparison with the composites based on either E-glass or low seed ECR-glass fibers even if the amounts of moisture absorbed by these composites are very similar. Since ECR-glass fiber composites are being considered for high voltage insulator applications due to their very high resistance to brittle fracture, the presence of seeds could significantly reduce the insulation properties of the insulators and thus causing electrical failures by flashovers. Therefore, all new composites can be screened for moisture and leakage currents and their moisture/leakage current factor, $F_{M-LC}$, determined and compared with some standard data. The testing methodology described herein appears to be the suited for this purpose considering the data shown in FIGS. 8a and 8b.

It is important to realize the benefits of performing such a systematic testing procedure on all possible materials used in high voltage composite insulators. By performing these experiments we can provide manufacturers and users of high voltage composite insulators with high quality guidelines for which materials should be used in different ambient conditions. There are, however, a wide variety of possible combinations of polymer resins and E-glass and ECR-glass fibers that should be tested to determine how these different composites will behave electrically in the presence of moisture.

The preceding experimental studies have investigated one of the best (ECR (low seed)-glass/epoxy) and most likely one of the worst (ECR (high seed)-glass/modified polyester) composite system available for high voltage insulator applications. It was found that there was a direct linear relationship between the amount of absorbed moisture and the leakage current. The ECR (low seed)-glasslepoxy material reacted very positively—low leakage currents with little increase—and the ECR (high seed)-glass/modified polyester materials reacted in a most unfavorable fashion showing considerable increase in leakage current as a function of absorbed moisture. Most importantly, however, is that due to this linear relationship between absorbed moisture and change in leakage current, we can accurately predict electrical insulation properties based on our knowledge of the moisture absorption properties of the composites. It was also shown that the moisture/leakage current factors, $F_{M-LC}$, of the two composites differed by approximately 150-200 times clearly indicating the supreme resistance of the ECR (low seed)-glass/epoxy system to the development of leakage currents in comparison with the ECR (high seed)-glass/modified polyester system. Most importantly, the testing procedure developed here has shown to be extremely useful in the determination of moisture and leakage currents under Fickian and anomalous diffusion conditions.

The present invention can be used, for example, as a screening method that will indicate potential problems associated with moisture absorption in some dielectrics. Different dielectrics (e.g., polymers, ceramics, wood, concrete, biomaterials and their composites based on a variety of classes of fibers and matrices, such as glass, silicon nitride and silicon carbide, polymers, and wood) can be ranked for their nearly simultaneous resistance to moisture and leakage currents. In particular, the present invention allows different insulator manufacturers and users to select the best insulating material (either neat or composites) for different electrical applications subjected to different environmental conditions. It will also allow manufacturers and users of these materials to monitor changes in the moisture/leakage current response as a function of time (time, damage, degradation, etc.). No other techniques presently available can be used successfully for these purposes.

For example, composite bushings could be tested for moisture and leakage currents. These bushings are based on multi-axis glass/polymer composites made by filament winding instead of pultrusion, which is generally applied in the production process of composite rods for suspension and substation insulators. The bushings are large diameter, small wall thickness, large composite structures. The diameter of the bushings can be as large as 1 meter and their length can be use to 10 meters with a wall thickness of a few millimeters. A short section of a bushing can be subjected to moisture, and leakage currents can be then measured using the present invention. The size of the electrodes 12 and 13, and the voltage level and ramp rate, and other dimensions shown in FIG. 1 would have to be modified to accommodate a much larger specimen 11. The numerical procedures for moisture diffusion and leakage currents would generally remain the same. Similarly, a wooden pole used as a support structure in a distribution system could be tested for its resistance to leakage currents in the presence of moisture.

It should also be understood that the present invention can also be applied to a dielectric materials that are subject to diffusion of another phase (other than moisture) that could affect its electrical properties. For example, one could evaluate the effect of a liquid metal being absorbed by a ceramic and thus changing its insulating properties. Numerous examples of this type can be imagined.

We claim:

1. A method for predicting long-term electrical insulation properties of materials in a moist environment, comprising the steps of:
   (a) providing a specimen;
   (b) testing the specimen to determine absorbed moisture content values and leakage current values of the specimen at predetermined time intervals;
   (c) determining a moisture-leakage current factor from the absorbed moisture content values and leakage current values; and
   (d) using the moisture-leakage current factor to determine electrical insulation properties of the specimen.

2. The method according to claim 1, and further including the step of determining moisture absorption properties of the specimen.

3. The method according to claim 2, and further including the step of predicting a maximum moisture content, a maximum leakage current, and a time to saturation.

4. The method according to claim 1, wherein the moisture-current leakage factor is determined from a graph of change in leakage current values versus moisture content values.

5. The method according to claim 4, wherein a linear relationship exists between the leakage current values and the moisture content values.

6. The method according to claim 1, and further including the step of subjecting the specimen to a diffusible material.

7. The method according to claim 1, and further including the step of subjecting the specimen to a high voltage.

8. The method according to claim 7, wherein the voltage is ramped up to a maximum voltage of between about 5 Volts per millimeter of specimen length and about 500 Volts per millimeter of specimen length.

9. A method for predicting long-term electrical insulation properties of composite materials in a moist environment, comprising the steps of:
   (a) providing a specimen in the form of a hollow-core cylinder;
   (b) exposing the cylinder to a diffusible material;
   (c) at predetermined intervals:
      (i) measuring a moisture content of the cylinder due to absorption of the diffusible liquid; and
      (ii) subjecting the cylinder to a high voltage and measuring a leakage current in the cylinder;
   (d) determining a moisture-leakage current factor from the moisture content and leakage current; and
   (e) correlating the moisture-leakage current factor to standardized data to determine electrical insulation properties of the specimen.

10. The method according to claim 9, and further including the step of placing the cylinder in an environmental chamber and maintaining the cylinder at a constant temperature and a constant humidity.

11. The method according to claim 9, and further including the step of weighing the cylinder to determine the moisture content.

12. The method according to claim 9, and further including the step of measuring an initial mass of the cylinder prior to subjecting the cylinder to the diffusible material.

13. The method according to claim 9, and further including the step of measuring an initial leakage current of the cylinder prior to subjecting the cylinder to the diffusible fluid.

14. The method according to claim 9, and further including the step of predicting a maximum moisture content, a maximum leakage current, and a time to saturation using an anomalous diffusion model.

15. The method according to claim 9, wherein the moisture-current leakage factor is determined from a graph of change in leakage current versus moisture content.

16. The method according to claim 15, wherein a linear relationship exists between the leakage current and the moisture content.

17. The method according to claim 9, wherein the diffusible material is selected from the group consisting of water, liquid metal, liquid solutions, and vapors.

18. A method for predicting long-term electrical insulation properties of composite materials in a moist environment, comprising the steps of:
   (a) providing a specimen in the form of a hollow-core cylinder;
   (b) recording an initial mass of the cylinder;
   (c) recording an initial leakage current of the cylinder;
   (d) placing the cylinder in an environmental chamber;
   (e) subjecting the cylinder to a diffusible fluid;
   (f) removing the cylinder from the environmental chamber at predetermined time intervals and recording a mass and a leakage current of the cylinder;
   (g) determining a moisture content of the cylinder from the mass of the cylinder;
   (h) determining a moisture-leakage current factor from the moisture content and leakage current; and
   (i) using the moisture-leakage current factor to determine electrical insulation properties of the specimen.

19. The method according to claim 18, and further including the step of placing the cylinder in a high voltage chamber and subjecting the cylinder to a high voltage.

20. The method according to claim 18, and further including the step of subjecting the cylinder to a high voltage.

21. The method according to claim 18, wherein the environmental chamber maintains the cylinder at a constant temperature and a constant humidity.

22. The method according to claim 21, wherein the temperature is maintained between about 20 and about 100 degrees Celsius and the humidity is maintained between about 10 and about 100 percent relative humidity.

23. The method according to claim 18, and further including the step of correlating a rate of moisture absorption to a rate of increase in leakage currents using the equation $$I_{L(AC)}(t) = F_{M-LC} \cdot M(t).$$

24. The method according to claim 18, wherein the cylinder has a length of about 0.1 millimeters to about 50 millimeters.

25. The method according to claim 18, wherein the cylinder has an outside diameter of about 2 millimeters to about 100 millimeters.

26. The method according to claim 18, wherein the cylinder has an inside diameter of about 1 millimeter to about 99 millimeters.

27. The method according to claim 18, and further including the step of placing the cylinder between two electrodes.

28. The method according to claim 27, and further including the step of subjecting the cylinder to a high voltage.

29. The method according to claim 28, wherein the voltage is ramped up to a maximum voltage of between about 5 Volts per millimeter of specimen length and about 500 Volts per millimeter of specimen length.

* * * * *